United States Patent [19]

Hearn

[11] Patent Number: 5,755,721

[45] Date of Patent: May 26, 1998

[54] PLATE HOLDING DRILL GUIDE AND TROCAR AND METHOD OF HOLDING A PLATE

[75] Inventor: James P. Hearn, Claymont, Del.

[73] Assignee: Synthes, Paoli, Pa.

[21] Appl. No.: 614,629

[22] Filed: Mar. 13, 1996

[51] Int. Cl.⁶ ............................ A61B 17/17; A61B 17/58
[52] U.S. Cl. .............................. 606/96; 606/79; 606/80; 606/86; 606/104; 606/69
[58] Field of Search ............................ 606/96, 79, 80, 606/86, 98, 104, 69

[56] References Cited

U.S. PATENT DOCUMENTS

| | | | |
|---|---|---|---|
| 3,604,487 | 9/1971 | Gilbert | 145/50 |
| 5,507,801 | 4/1996 | Gisin et al. | 606/96 |
| 5,569,256 | 10/1996 | Vaughn et al. | 606/80 |

*Primary Examiner*—Michael Buiz
*Assistant Examiner*—Daphna Shai
*Attorney, Agent, or Firm*—Fish & Richardson P.C.

[57] ABSTRACT

A plate holding drill guide or "trocar" is disclosed including a member having a channel with an internal diameter. A cannulated holding member having prongs is disposed, at least in part, within the channel. A cannula extends through the prongs. At one end, the prongs are flanged outward. The flanged portion has an external diameter which is greater than the internal diameter of the channel. The sliding member is displaceable over the flanged portion of the prongs. When an annular frame of a bone plate is disposed between the prongs and the sliding member is moved toward the flanged portion, the prongs grip the frame. A drill may be guided between the prongs through the cannula. A method is disclosed for holding a bone plate. An annular frame of the bone plate is positioned between prongs and aligned with a cannula extending between the prongs. A member is displaced along the prongs. The prongs are deflected inward, gripping the frame.

17 Claims, 5 Drawing Sheets

5,755,721

PLATE HOLDING DRILL GUIDE AND TROCAR AND METHOD OF HOLDING A PLATE

FIELD OF THE INVENTION

The invention relates generally to the placement of bone plates used in the reduction and compression of fractures and nonunions where the bones or fragments are small and the working space for the surgeon is cramped. These plates must be maintained at a specific position on the bone while a hole is drilled and a screw is driven into the bone. The drill must be maintained at a specific orientation with respect to the plate to insure that the screw head seats properly in the plate. The invention relates specifically to a drill guide having prongs which firmly grip an annular frame of a bone plate while permitting the drill to drive a bit or a screw through the annular frame at a selected orientation.

BACKGROUND OF THE INVENTION

In orthopedics, successful treatment of nonunion and fractures of small bone fragments, particularly in maxillofacial surgery, often involves the use of small bone plates having a series of annular frames connected by rectangular struts. The bone plates must be positioned with great accuracy on the bone. However, drilling holes and driving screws into the bone requires both hands of the surgeon: one to operate the drill and one to operate a drill guide. Consequently, an assistant must position the bone plate. There is often little space for the surgeon to operate, making it difficult for the assistant to maintain the plate in place without interfering with the surgery.

Standard clamps, operating in plier-like fashion, have been used to hold the bone plate in position in this application. The tips of the clamp grip the bone plate at the strut between two annular frames. A clasp maintains the clamp in this closed position. An assistant must manipulate the clamp to hold the plate in the position desired by the surgeon, while the surgeon drills the holes and sinks the screws. The clamps are large, often interfering with the operation of the drill and the drill guide, as well as the field of vision of the surgeon. The clamp requires a separate hand to operate it, thus requiring that an assistant be in the operating field, further interfering with the surgeon. Even when the plate is held in position properly, the drill guide is not fixed to the plate. Consequently, the drill guide can change its orientation with respect to the plate, resulting in the misplacement of the drill and any drilled holes. Since there may be a small amount of bone available for sinking a screw, such misplacement can be critical. Further, the screw head may not be well seated in the plate, resulting in irritation to adjacent soft tissue.

SUMMARY OF THE INVENTION

It is an object of this invention to provide a drill guide which permits the surgeon to position the bone plate as well as to orient and operate the drill.

It is a further object of the invention to provide a drill guide which will hold the bone plate firmly in position on the bone during drilling without the need for a separate clamp.

It is a further object to provide a drill guide which will maintain the bone plate in a fixed orientation with respect to the drill guide while the bone is being drilled.

It is a further object of the invention to provide a method of positioning a bone plate which permits the surgeon to orient and operate the drill as well.

It is a further object of the invention to provide a method of maintaining a bone plate in a desired position on the bone while drilling without the need for a separate clamp.

It is a further object of the invention to provide a method for fixing the orientation of a bone plate with respect to a drill guide while a bone is being drilled.

The noted drawbacks of existing means of holding bone plates while drilling are overcome by use of the plate holding drill guide and method of the present invention. In accord with one aspect of the invention, the drill guide includes a sliding member having a channel with an internal diameter. A cannulated holding member having prongs is disposed, at least in part, within the channel. At one end, the prongs spread outward. The spread portion has an external diameter which is greater than the internal diameter of the channel. The sliding member is displaceable over the spread portion of the prongs. When an annular frame of a bone plate is disposed between the prongs and the sliding member is moved toward the spread portion, the prongs are deflected inward and grip the frame. The drill may be guided between the prongs through the cannula.

In another aspect of the invention, a method is provided for positioning a bone plate. An annular frame of the bone plate is positioned between free ends of prongs. A sliding member is displaced along the prongs causing the prongs to be deflected inwardly and to grip the frame.

The drill guide can be used to hold the plate and to guide the drill. The plate is retained in a fixed orientation with respect to the drill guide, ensuring that the screw is well seated in the frame. Consequently, the surgeon is able to position the plate on the bone as well as orient and operate the drill, without delegating these tasks to an assistant. Further, there is one less tool in the operating field.

DESCRIPTION OF THE DRAWINGS

The invention will be disclosed more fully in connection with the accompanying drawings in which.

DETAILED DESCRIPTION

Figure 1:
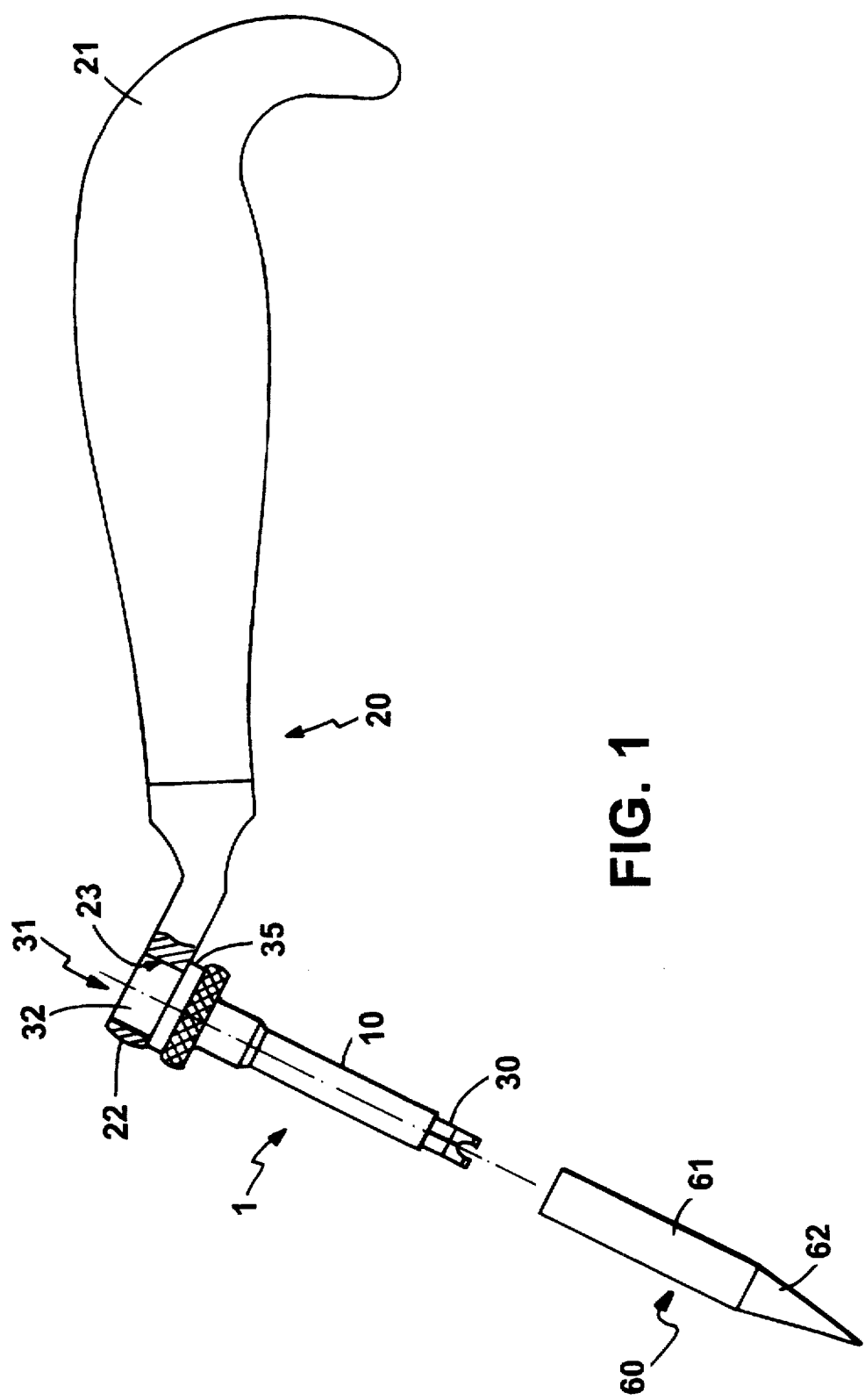
FIG. 1 is a side elevation view in partial cross section of a plate holding drill guide or trocar according to one aspect of the invention, shown attached to a handle.

As shown in FIG. 1, a plate holding drill guide 1 or "trocar" according to one aspect of the invention includes a sliding member, such as sleeve 10, slidingly mounted on a holding member, such as tube 30. A cannula 31 extends completely through the tube and thus enables the tube to operate as a drill guide. A wire tap or a screw may be driven through the cannula at the orientation and location determined by the surgeon. The known length of the cannula (which is the length of the tube) can be employed to set the length of the drilled hole, as is known in the art.

Figure 2:
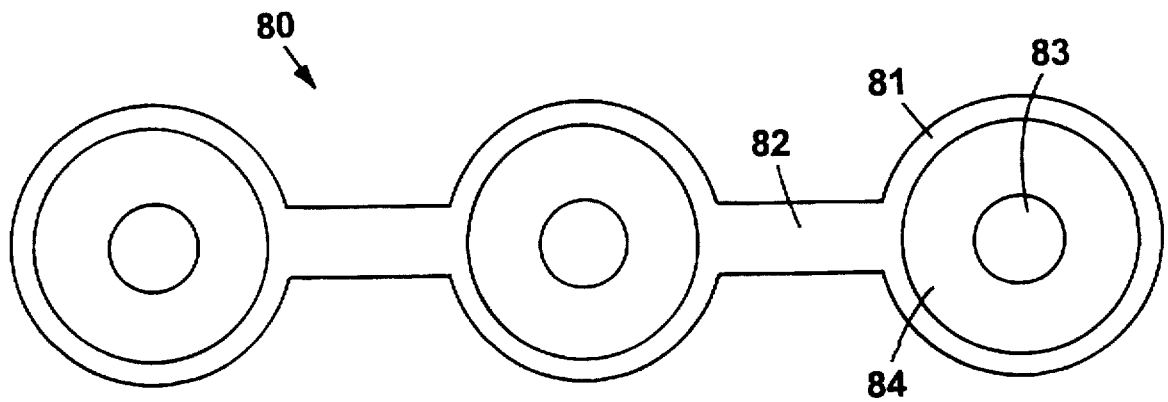
FIG. 2 is a top elevation view of a bone plate with which the drill guide of FIG. 1 can be used.

The drill guide 1 of FIG. 1 may be used with a bone plate, such as the bone plate 80 shown in FIG. 2. A series of annular frames 81 are connected by rectangular struts 82. Openings 83 are located in the center of the annular frames. The surface 84 of the frame surrounding the opening may be beveled to seat a screw head. The frames and struts may have many different arrangements depending on the particular application.

Figure 3:
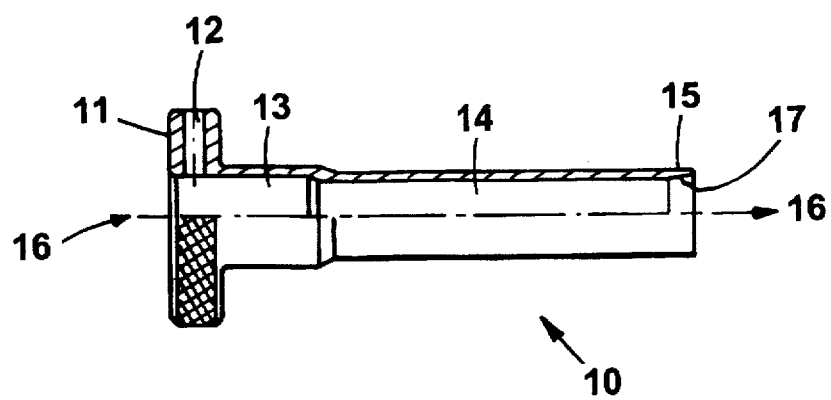
FIG. 3 is a side elevation view in partial cross section of a sleeve of the drill guide of FIG. 1, shown in isolation.

The sleeve 10 of FIG. 1 is shown in more detail in FIG. 3. It comprises a cylindrical body having a knurled flange 11 integrally formed therewith. Alternatively, the flange can be mounted on the sleeve by other means known in the art. A radially extending hole 12 is disposed in the knurled flange. As shown more clearly in FIG. 6, a pin 46 is driven into the hole 12 and projects into the interior of the sleeve. As discussed below, when assembled, the pin engages a helical track 36 on the tube 30.

A channel 16 having a circular cross section extends completely through the sleeve 10. The channel is cylindrical at portion 13 of the sleeve near the knurled flange, is tapered inwardly, and then is cylindrical in portion 14 of the sleeve remote from the knurled flange. The portion 14 remote from the knurled flange has a smaller diameter than the portion 13 near the knurled flange. The shape of the channel 16 is designed to accommodate the tube 30 for telescoping movement. Of course, other shapes could be employed which permit sliding between the tube and the sleeve. At the end 15 of the sleeve 10 remote from the flange 11, the sleeve wall thins, the interior of the wall slanting slightly outward and forming a ramp 17 on the interior of the sleeve wall.

Figure 4:
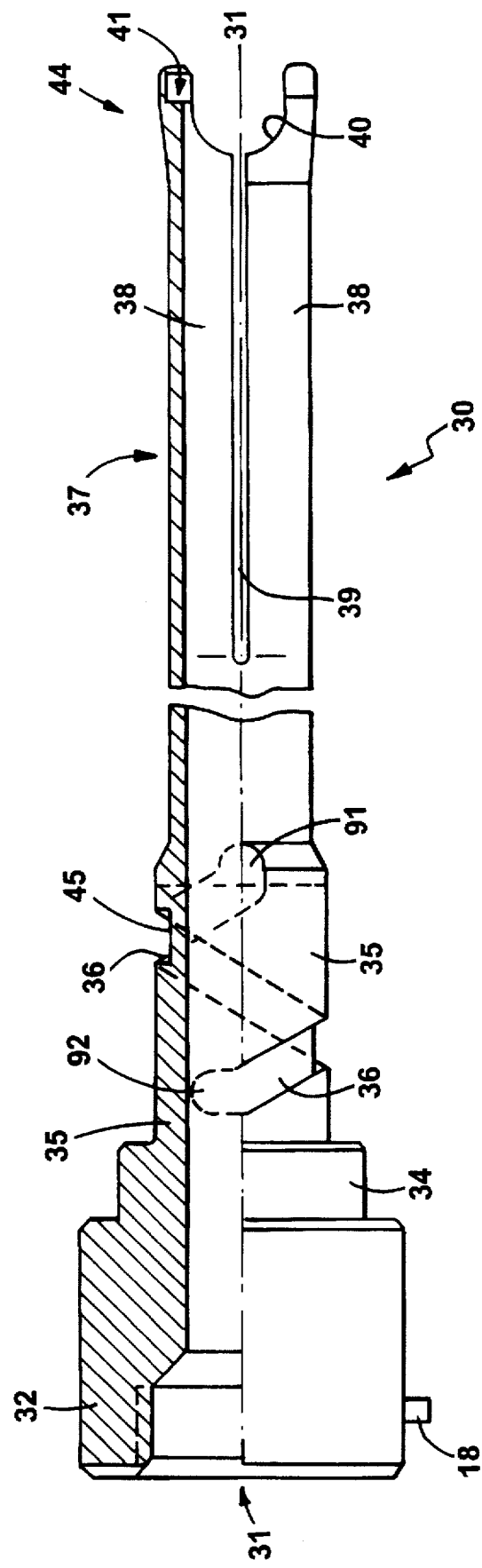
FIG. 4 is a side elevation view in partial cross section of a tube of the drill guide of FIG. 1, shown in isolation.

The structure of tube 30 is shown more clearly in FIG. 4. As shown there, the tube 30 has a free end 37. A cylindrical head 32 is positioned coaxially with the tube at the end of the tube 30 remote from the free end. A cylindrical tab 18 extends radially from the head 32. The cannula 31 extends through the tube 30 from the head 32 to the free end 37 and is positioned coaxially with the tube. A cylindrical shoulder 34, having an outer diameter less than that of the head, is disposed coaxially with and adjacent to the head. An annular body, such as collar 43 (see FIG. 6), having an outer diameter greater than that of the head 32, may be mounted on or integrally formed with the shoulder. A region 35 of increased wall thickness is disposed adjacent the shoulder. The outer diameter of the region of increased wall thickness is less than that of the shoulder 34.

A helical track 36 (shown in partial phantom in FIG. 4) is located at the exterior of the tube in the region 35 of increased wall thickness. At the end 92 of the track near the head, the track travels directly circumferentially. At the end 91 of the track near the free end 37, the track travels directly axially. The depth of the track is selected such that the base 45 of the track has the same diameter as the free end 37 of the tube.

Parallel slots 39 are disposed in the free end 37 of the tube 30, forming prongs 38. The prongs form a part of the wall of the cannula 31. The prongs are elastic, at least to some extent, so that they can flex toward or away from the axis of the cannula. Since the annular frames 81 of the bone plate have curved sides, a curved shape is preferred for the prongs in this application. However, the prongs can be shaped to fit the sides of other frames as the particular application dictates. Of course, there could be different numbers of prongs and the prongs could be fixed with respect to each other in different manners without departing from the invention. For example, a single slot may be disposed in the tube, creating a single curved prong which can be deflected to grip a bone plate in accord with the invention.

The tips of the prongs 38 have an increased wall thickness, forming a flanged or spread portion 44. The external diameter of the flanged portion is greater than the external diameter of the rest of the prong. The prongs 38 also can be deformed outwardly to create the increased external diameter of the flanged portion. However formed, the external diameter of the flanged or spread portion of the prongs is greater than the internal diameter of the end 15 of the sleeve 10.

A ledge 41 is formed at the interior of the flanged portion 44 of the prongs 38. The ledge provides a circular seat, perpendicular to the axis of the cannula 31. As discussed below, the annular frame 81 of the plate 80 is seated on the ledge 41 when it is gripped by the prongs 38. Consequently, the ledge orients the plate with respect to the drill guide 1, aligning the cannula 31 with the opening 83 in the annular frame.

Notches 40 are located between the tips of the prongs 38 by expanding the width of the slots 39. The notches are sized to accept the struts 82 connecting adjacent annular frames 81 of the bone plate 80.

Figure 6:
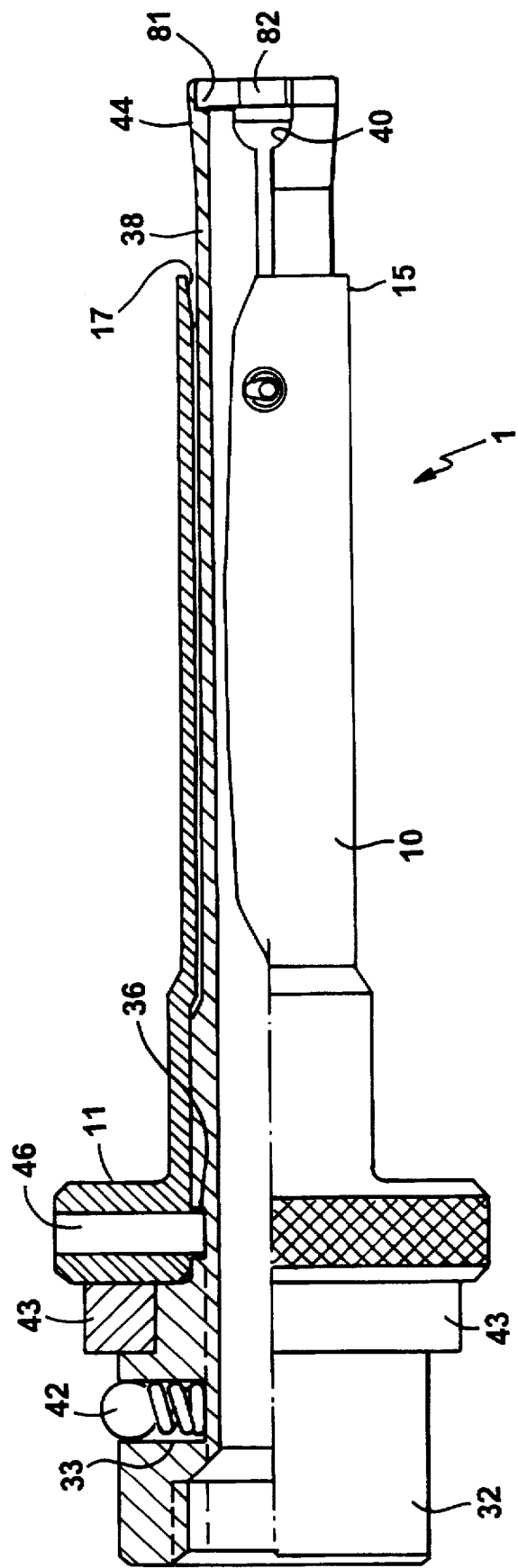
FIG. 6 is a side elevation view in partial cross section of the drill guide of FIG. 1.

As seen in FIG. 6, a cylindrical detent chamber 33 is formed in the head 32 of the tube 30 and extends radially outwardly. A spring and ball detent 42 is seated in the chamber.

Referring to FIG. 1, a handle 20, including a grip 21 and a retainer 22, may be employed to help the surgeon control the drill guide 1 and position any secured plate. Both the drill guide and the handle may be made of stainless steel. The head 32 of the drill guide is engaged in an opening 23 in the retainer 22. Preferably, the drill guide is releasably seated in the retainer, permitting the use of different size drill guides with a single handle, or the use of different handles with a single drill guide, as the particular application requires.

Figure 5:
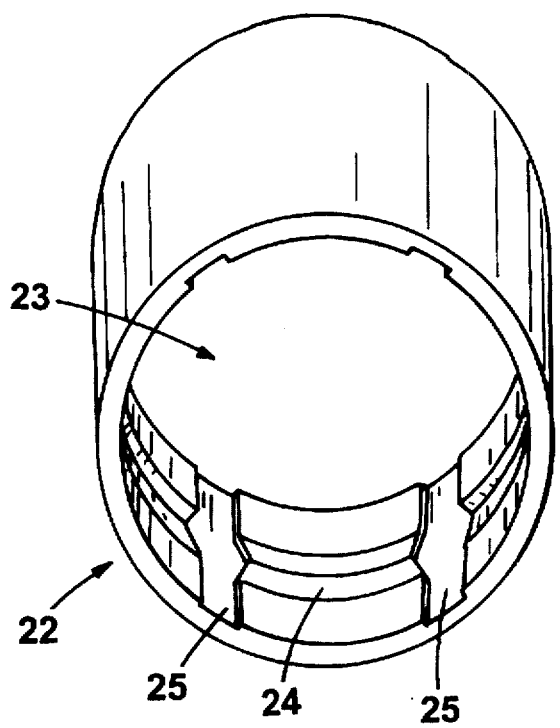
FIG. 5 is a perspective view from the bottom of a retainer of the handle.

The retainer 22 is shown in detail in FIG. 5. It is a cylindrical body, in whose inner wall lies a depression 24 extending circumferentially around the body near the bottom. Four evenly spaced journals 25 extend longitudinally along the wall of the opening. The tab 18 on the head 32 (see FIG. 4) is displaced circumferentially from the detent chamber 33 (see FIG. 6) so that the detent 42 will not align with a journal 25 in the retainer 22 when the tab is aligned with a journal.

To operate the drill guide 1 or "trocar" of the present invention, the tube 30 is inserted into the sleeve 10. The pin 46 slides over the free end 37 of the tube. The sleeve is rotated until the pin aligns with the axial portion 91 of the track 36, at which point the pin slides into the track. As the pin travels in the helical portion of the track, the sleeve 10 is caused to rotate about the tube 30 and move toward the head 32 until the knurled flange 11 of the sleeve contacts the collar 43 of the tube, preventing further movement. At this point (shown in FIG. 6), the flanged portion 44 of the prongs 38 extend out of the sleeve 10 and the prongs expand to the flanged out or spread position.

The tab 18 on the head 32 is aligned with one of the journals 25 in the opening 23 of the retainer 22. The head is inserted into the opening until the detent 42 engages the depression 24. Any convenient number of journals can be provided to permit the surgeon to select a comfortable orientation. Of course, other means of selectively or permanently attaching the drill guide 1 to the handle 20 could be employed, such as threading or welding the head to the opening.

A cover 60 may be positioned over the drill guide 1 to displace soft tissue covering the bone. The cover is a cylindrical tube 61 with a conical tip 62. The interior of the cover is sized to envelope the sleeve 10 and to be maintained in position by friction. Of course, other means of attaching the cover 60 to the sleeve 10 may be employed, such as threading the cover to the sleeve. Once the bone is exposed sufficiently, the cover is removed and the drill guide operated as discussed below. Soft tissue retractors, such as cheek retractors and the like, may be employed with the drill guide 1 for a particular application, as those skilled in the art will appreciate.

As seen in FIG. 6, the annular frame 81 of a bone plate 80 is positioned between the prongs 38 and seated against the ledge 41. The struts 82 connecting the frames are positioned in the notches 40. The prongs 38 should be sized such that the internal diameter of the prongs at the flanged portion 44 is slightly greater than the exterior diameter of the annular frame 81. For example, when the annular frame has an external diameter of 3 mm, the prongs should be separated by 4 mm. The interior diameter of the end 15 of the sleeve 10 is 3.5 mm.

The knurled flange 11 is rotated, causing the pin 18 to travel in the track 36. As the pin travels, the sleeve 10 is displaced away from the head 32 and slides over the prongs 38. The ramp 17 at the interior of the sleeve 10 contacts the flanged portion 44 of the prongs. As the ramp slides over the flanged portion, the prongs 38 are forced together, causing the prongs to tightly grip the frame 81. Friction between the ramp and the flanged portion operates as a lock, maintaining the sleeve 10 on the flanged portion. Consequently, the frame 80 is maintained in a constant position with respect to the drill guide 1. Other means for displacing a sliding member, such as the sleeve 10, over the holding member could be employed without departing from the invention. For example, a ring could be pushed directly along the tube 30 and over the prongs 38.

The surgeon, holding the grip 21, then positions the plate 80 to establish the location of the first screw. The drill bit is inserted through the cannula 31 and drilled into the bone. After the hole is drilled and the drill bit is removed, a standard implant screw can be driven into the bone through the cannula. Once the screw is in place, the knurled flange 11 may be rotated back, withdrawing the sleeve 10 from the flanged portion 44 of the prongs 38, allowing the prongs to spread out and releasing the annular frame 81. If necessary, the plate 80 may be rotated into position for drilling of the remaining screws. If desired, the drill guide 1 may be clamped onto other annular frames for the drilling and driving of screws into the other annular frames.

Figure 7:
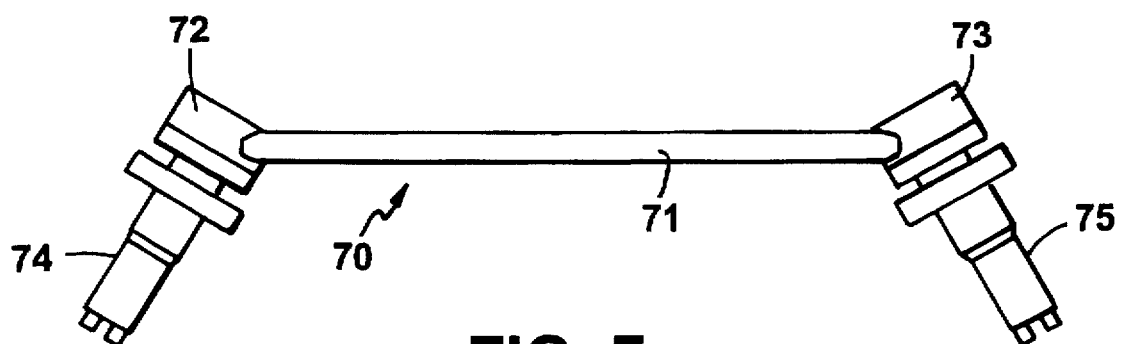
FIG. 7 is a side elevation view of the drill guide of FIG. 1 mounted on an alternative handle.

FIG. 7 shows another handle 70 for use with the drill guide 1 of the current invention. A flat member 71 has a retainer 72,73 mounted at each end. The retainers are angled to provide a more convenient grip to the surgeon. Drill guides 74,75 of different sizes may be retained in each retainer, permitting the surgeon to change annular frame sizes by merely turning the drill guide handle 70 around.

The foregoing description of an embodiment of the invention is in no way intended as a limitation on the invention which is defined by the following claims:

I claim:

1. An apparatus for holding a bone plate comprising:
    a sliding member having a channel with an internal diameter; and
    a holding member having a free end and prongs which spread apart and which have a continuously flanged portion extending to the free end, the flanged portion having an external diameter greater than the internal diameter of the channel, the holding member being disposed, at least in part, within the channel, and the sliding member being slidable along the prongs to contact the flanged portion and to close the prongs such that the prongs are capable of an interlocking engagement with an annular frame of the bone plate.

2. The apparatus of claim 1 wherein the holding member is cannulated.

3. The apparatus of claim 1 wherein the prongs are mounted on a tube.

4. The apparatus of claim 3 wherein the prongs are formed by slots in the tube.

5. The apparatus of claim 3 wherein the sliding member is a sleeve telescoped about the tube.

6. The apparatus of claim 1 further comprising a means for displacing the sliding member with respect to the prongs.

7. The apparatus of claim 6 wherein the displacing means comprises a track on the holding member and a rider mounted on the sliding member.

8. The apparatus of claim 7 wherein the prongs are mounted on a tube and wherein the displacing means comprises a helical track mounted on the tube and the rider comprises a pin mounted on the member.

9. The apparatus of claim 1 further comprising a handle selectively engaged with the holding member.

10. The apparatus of claim 9 wherein the holding member includes a tube attached to the prongs and a detent mounted on the tube, an opening having a depression being disposed in the handle, at least a portion of the tube being disposed in the opening and the detent being engaged with the depression.

11. The apparatus of claim 1 further comprising a handle having two retainers, the holding member being selectively engaged with one retainer.

12. A plate holding drill guide comprising:
    a tube having a free end and a head, a cannula extending through the tube from the head to the free end, the free end being spread outwardly and having an external diameter;
    a hollow sleeve having an internal diameter less than the external diameter of the free end, the sleeve enveloping the tube for telescoping movement from a first position near the head to a second position near the free end; and
    at least one prong which is continuously flanged outwardly and extends to the free end of the tube, and wherein the at least one prong is enclosed, at least in part, within the sleeve when the sleeve is in the second position.

13. The drill guide of claim 12 further comprising a helical track mounted on the tube and a pin mounted on the sleeve and engaging the track.

14. The drill guide of claim 12 further comprising a knurled flange mounted on the sleeve.

15. The drill guide of claim 12 wherein the at least one prong is formed by at least one slot in the tube and a notch is disposed at the free end of the tube at the slot.

16. The drill guide of claim 12 further comprising a detent mounted on the tube and a handle selectively attached to the tube by the detent.

17. An apparatus for holding a bone plate and guiding a drill comprising:
    a tube having a cannula, a free end and a second end;
    a sleeve telescoped about the tube, the sleeve having an internal diameter;
    a pin mounted on the sleeve and extending into the interior of the sleeve;
    a spiral track formed on the surface of the tube at the second end of the tube, said pin being seated in said track; and
    slots at the free end of the tube remote from the track, the slots forming continuously outwardly flanged prongs extending to the free end of the tube, the external diameter of the prongs being greater than the internal diameter of the sleeve, wherein the sleeve is slidable along the flanged prongs and the prongs are capable of an interlocking engagement with an annular ring in the bone plate.

* * * * *